United States Patent [19]

Sato

[11] Patent Number: 4,677,216
[45] Date of Patent: Jun. 30, 1987

[54] 2-SUBSTITUTED-1,3-BUTADIENE DERIVATIVES AND PROCESS FOR PRODUCING SAME

[75] Inventor: Fumie Sato, Chigasaki, Japan

[73] Assignee: Nissan Chemical Industries, Ltd., Tokyo, Japan

[21] Appl. No.: 704,088

[22] Filed: Feb. 22, 1985

[30] Foreign Application Priority Data

Feb. 24, 1984 [JP] Japan ................................ 59-33733
Dec. 25, 1984 [JP] Japan ............................... 59-277154

[51] Int. Cl.$^4$ ............................ C07F 7/08; C07F 7/18
[52] U.S. Cl. ................................... 556/482; 556/465; 556/475; 556/479; 556/480; 556/484
[58] Field of Search ............... 556/475, 465, 479, 480, 556/482, 484

[56] References Cited

U.S. PATENT DOCUMENTS

| | | | |
|---|---|---|---|
| 2,380,057 | 7/1945 | McGregor et al. | 556/480 |
| 2,426,121 | 8/1947 | Rust et al. | 556/480 |
| 2,637,738 | 5/1953 | Wagner | 556/465 X |
| 2,640,031 | 5/1953 | Fano | 556/471 X |
| 2,671,101 | 5/1953 | Frisch et al. | 556/480 X |
| 2,736,736 | 2/1956 | Pines et al. | 556/475 |
| 2,752,380 | 6/1956 | Wagner et al. | 556/475 |
| 2,823,218 | 2/1958 | Speier et al. | 556/479 X |
| 3,008,975 | 11/1961 | Schubert | 556/471 X |
| 3,425,983 | 2/1969 | Wolfe | 556/475 UX |
| 4,268,682 | 5/1981 | Oswald et al. | 556/465 |
| 4,347,376 | 8/1982 | Baum et al. | 556/475 X |

OTHER PUBLICATIONS

Noll, "Chemistry and Technology of Silicones", Academic Press, N.Y. (1968), pp. 42-43, 50-51, 81, and 134-135.
Batt et al., Tetrahedron Letters, No. 36, pp. 3323-3324.
Chemical Abstracts, vol. 98, No. 5, p. 617, No. 34178c (Jan. 31, 1983).
Chemical Abstracts, vol. 102, No. 3, p. 703, No. 24705j (Jan. 21, 1985).

Primary Examiner—Paul F. Shaver
Attorney, Agent, or Firm—Birch, Stewart, Kolasch & Birch

[57] ABSTRACT

A novel 2-substituted-1,3-butadiene compound which may be used as a coupling agent is disclosed, i.e. a 2-substituted-1,3-butadiene compound of the general formula (I)

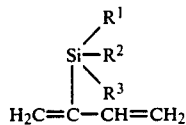

in which $R^1$, $R^2$ and $R^3$ independently represent a halogen, a lower alkyl group, or a lower alkoxy group with the exception of those compounds wherein $R^1$, $R^2$ and $R^3$ are all lower alkyl groups.

10 Claims, No Drawings

2-SUBSTITUTED-1,3-BUTADIENE DERIVATIVES AND PROCESS FOR PRODUCING SAME

BACKGROUND OF THE INVENTION

1. Field of the Invention

This invention relates to novel butadiene derivatives and more particularly, to novel 2-substituted-1,3-butadiene compounds. The invention also relates to a process for producing the novel compounds.

2. Description of the Prior Art

It is known that 2-triethylsilyl-1,3-butadiene is prepared by a process which comprises the steps of reacting 1,4-dichloro-2-butyne and triethylsilane to obtain 2-triethylsilyl-1,4-dichloro-2-butene, and subjecting the butene to dechlorination in an alcohol (Tetrahedron Letters, Vol. 36, Page 3323). However, this process is disadvantageous in that it cannot be applied to the production of 1,3-butadiene derivatives having a silyl substituent which is, in turn, substituted with either a combination of a halogen and an alkoxy group, or a combination of an alkoxy group and an alkyl group, etc.

SUMMARY OF THE INVENTION

It is accordingly an object of the present invention to provide novel 2-substituted-1,3-butadiene compounds including those having a silyl group substitued with a halogen and an alkoxy group, or an alkoxy group and an alkyl group.

It is another object of the invention to provide novel 2-substituted-1,3-butadiene compounds which are very useful as silane coupling agents.

It is a further object of the invention to provide a process for producing the novel 2-substituted-1,3-butadiene compounds.

According to the present invention, there is provided a 2-substituted-1,3-butadiene compound of the following general formula (I)

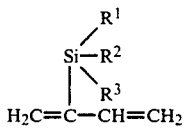

[I]

in which $R^1$, $R^2$ and $R^3$ independently represent a halogen, a lower alkyl group, or a lower alkoxy group with the exception of those compounds wherein $R^1$, $R^2$ and $R^3$ are all lower alkyl groups.

The compound of the formula (I) can be prepared by two different processes. One of the processes comprises dehalogenating the halogen atoms at the 1 and 4 positions of a 2-substituted-1,4-dihalogeno-2-butene of the following formula (II)

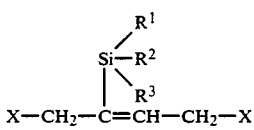

[II]

in which $R^1$, $R^2$ and $R^3$ have the same meanings as defined above, and X represents a halogen, in a non-alcoholic solvent, e.g. a cyclic ether, thereby obtaining the compound of the formula (I).

If it is desired to obtain the compound of the formula (I) in which at least one of the three substituents is a halogen and the other substituents are independently a lower alkyl group or a lower alkoxy group, the following sequence of reactions are used. For convenience sake, the more specified compound is represented by the following formula (Ia)

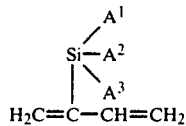

[Ia]

in which at least one of $A^1$, $A^2$ and $A^3$ represents a halogen and the others independently represent a lower alkyl group or a lower alkoxy group. This compound (Ia) is prepared by a procedure which comprises the steps of reacting 1,4-dihalogeno-2-butyne of the formule (III)

$$X-CH_2-C\equiv C-CH_2X \quad [III]$$

in which X represents a halogen, with a compound of the formula (IV)

[IV]

in which at least one of $A^1$, $A^2$ and $A^3$ is a halogen and the others independently represent a lower alkyl group or a lower alkoxy group, thereby obtaining a compound of the formula (IIa)

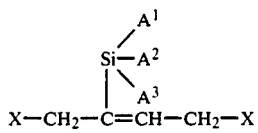

[IIa]

in which X, $A^1$, $A^2$ and $A^3$ have the same meanings as defined above, respectively, and subjecting the compound of the formula (IIa) to dehalogenation of the halogen atoms at the 1 and 4 positions thereof to obtain the compound of the above formula (Ia).

The compound of the formula (Ia) may be further reacted with a lower alcohol preferably in the presence of a base such as triethylamine to obtain a 2-substituted-1,3-butadiene compound of the following formula (Ib)

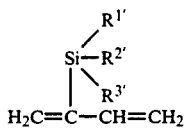

[Ib]

in which at least one of $R^{1'}$, $R^{2'}$ and $R^{3'}$ represents a lower alkoxy group, and the others represent a lower alkyl group. As a matter of course, the compound of the formula (Ib) is included within the scope of the more generic compound of the general formula (I).

The compound of the formula (Ib) may be prepared by another procedure which comprises, after formation of the compound of the formula (IIa), reacting the compound of the formula (IIa) with a lower alcohol so that the halogen atoms joined to the silicon atom at the 2 position of the compound are substituted with lower alkoxy groups to give a compound of the following formula (IIb)

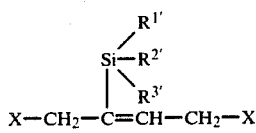
[IIb]

in which $R^{1'}$, $R^{2'}$, $R^{3'}$ and X have the same meanings as defined before, and subjecting the compound (IIb) to dehalogenation of halogens at the 1 and 4 positions thereof, thereby obtaining the compound of the above formula (Ib).

Another process for preparing the novel compound (I) is then described.

In this process, a magnesium 2-substituted-1,3-butadienylhalide of the following formula (V)

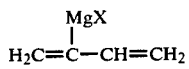
[V]

in which X represents a halogen, is reacted with a silane compound of the following formula (VI)

$$SiR^1R^2R^3R^4 \quad [VI]$$

in which $R^1$, $R^2$ and $R^3$ have the same meanings as defined before, respectively, i.e. they independently represent a halogen, a lower alkyl group or a lower alkoxy group with the exception of those compounds wherein $R^1$, $R^2$ and $R^3$ are all lower alkyl groups, and $R^4$ represents a halogen or a lower alkoxy group, thereby obtaining the compound of the formula (I). This process is economically advantageous because 2-substituted-1,3-butadienyl magnesium halide compounds and silane compounds, which can be readily prepared, are used as the starting materials, the control of the reaction is easy, and the number of reaction steps is small.

The above and other objects, features and advantages of the present invention will be fully understood from the following description.

DETAILED DESCRIPTION OF THE INVENTION

Specific and preferable examples of novel 2-substituted-1,3-butadiene compounds of the formula (I) according to the invention include 2-(trimethoxy)silyl-1,3-butadiene, 2-(methoxydimethyl)silyl-1,3-butadiene, 2-(dimethoxymethyl)silyl-1,3-butadiene, 2-(trichloro)silyl-1,3-butadiene, 2-(dimethylchloro)silyl-1,3-butadiene, and the like. It should be noted in the invention that the lower alkyl group and the lower alkoxy group have 1 to 5 carbon atoms respectively and the halogen include chlorine, bromine and iodine.

Preparation of the novel compounds of the invention is described in detail.

As described before, the compounds of the formula (I) may be prepared, according to one of the processes of the invention, from starting 1,4-dihalogeno-2-butene compounds of the formula (IIa) which have, at the 2 position, a silyl group having at least one halogen substituent. The compounds of the formula (IIa) are prepared according to the following reaction formula A in which 1,4-dihalogeno-2-butyne compounds (III) are reacted with hydrosilanes of the formula (IV) having at least one halogen atom.

[Reaction Formula A]

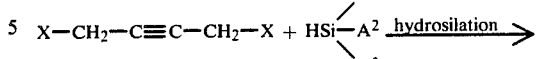

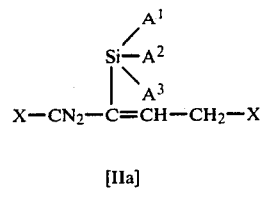

[IIa]

in which X represents a halogen, at least one of $A^1$, $A^2$ and $A^3$ represents a halogen, and the others independently represent a lower alkyl group or a lower alkoxy group.

Typical examples of the 1,4-dihalogeno-2-butene are 1,4-dichloro-2-butene. Preferably, the above reaction is carried out in the absence of any solvents but using, as a catalyst, chloroplatinic acid dissolved in a solvent such as isopropyl alcohol. The reaction temperature for the reaction A is from foom temperature to a boiling point of a hydrosilane used,

The reaction temperature is generally from about 30 minutes to 8 hours.

In the process of the invention in which the 1,4-dihalogeno-2-butene of the formula (IIa) is used as the starting material, the compound of the formula (IIa) is dehalogenated in a non-alcoholic solvent according to the following reaction formula B.

[Reaction Formula B]

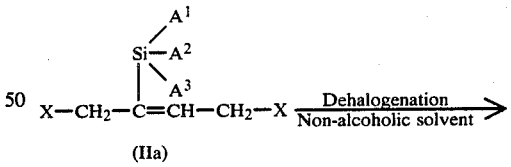

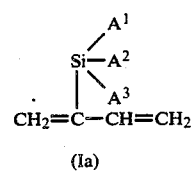

(Ia)

The compound of the formula (Ia) may be further reacted with a lower alcohol preferably in the presence of a base according to the following reaction formula C, so that the halogen atom or atoms joined to the silicon atom at the 2 position of the compound are substituted with a lower alkoxy group to obtain a compound of the following formula (Ib).

[Reaction Formula C]

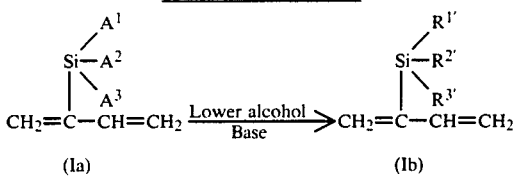

in which at least one of $A^1$, $A^2$ and $A^3$ is a halogen, the others independently represent a lower alkyl group or a lower alkoxy group, at least one of $R^{1'}$, $R^{2'}$ and $R^{3'}$ represents a lower alkoxy group, and the others independently represent a lower alkyl group, as defined before.

Alternatively, the compound of the formula (Ib) may be prepared according to the following reaction formula D. In the reaction formula D, the compound of the formula (IIa) is reacted with a lower alcohol preferably in the presence of a base to form a compound of the formula (IIb) in which the halogen atom jointed to the silicon atom at the 2 position thereof is substituted with the lower alkoxy group, followed by dehalogenation in nonalcoholic solvent to obtain a compound of the formula (Ib).

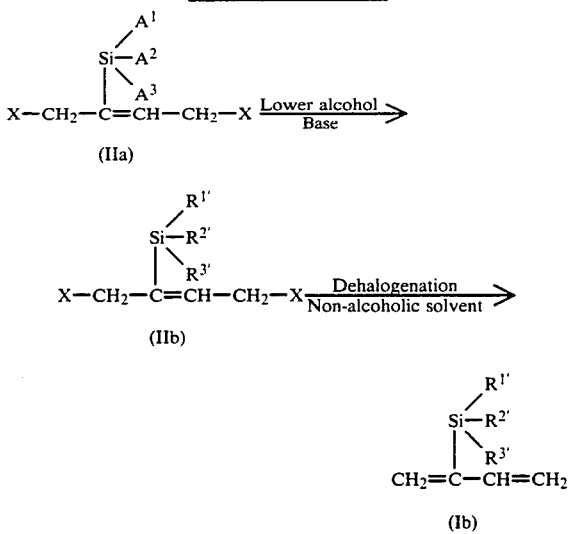

in which at least one of $R^{1'}$, $R^{2'}$ and $R^{3'}$ represents a lower alkoxy group and the others represent a lower alkyl group.

In the reaction formula B through D, the non-alcoholic solvents used for the dehalogenation reaction include, for example, cyclic ethers. Specific and preferable examples of such ethers include tetrahydrofuran (THF), dioxane and the like. In order to cause the dehalogenation reaction to proceed smoothly, it is preferable to use zinc powder or the like. It is also preferable to use zinc powder in combination with a zinc salt such as zinc chloride. The dehalogenation reaction is conducted at a temperature of from −10° C. to a boiling point of a non-alcoholic solvent used for a time of from 30 minutes to 8 hours. The amount of the non-alcoholic solvent is preferably in the range of 3 to 10 mols per mol of the starting compound.

The reaction of substituting a halogen atom joined to the silicon atom with a lower alkoxy group by reaction between a halogen and a lower alcohol proceeds smoothly when using a base, e.g. an organic aliphatic amine such as triethylamine. The substitution reaction is conducted under conditions of a reaction temperature of from −10° C. to 100° C. and a reaction time of from 30 minutes to 2 hours. Preferably, the amount of the lower alcohol is in the range of from 1.0 to 1.5 mols per mol of the starting compound and the amount of the amine is in the range of from 1.0 to 1.5 mols per mol of the starting material.

For the preparation of the compound according to the invention using the reaction procedures B through D, the reaction product obtained in one step may be used, as it is, in a subsequent step.

The process described above makes use of the dehalogenation reaction. This dehalogenation reaction is effected in a non-alcoholic solvent as is different from the process described in the afore-indicated literature (Tetrahedron Letters, Vol. 36, page 3323), so that the resulting product can be used in a subsequent step without a loss of the substituted silyl group having the reactive halogen.

Thus, 1,4-dichloro-2-butene having at least one halogen-substituted silyl group at the 2 position thereof or 1,3-butadiene having at least one halogen-substituted silyl group at the 2 position may be readily introduced, at the silyl group, with various substituents other than lower alkyl group and lower alkoxy groups by the use of the reactivity of the halogen of the halogen-substituted silyl group.

Another process for preparing the compounds of the present invention is described.

This process comprises reaction between magnesium 2-substituted-1,3-butadienyl halide of the formula (V) and a silane compound of the formula (VI) according to the following reaction formula (E).

[Reaction Formula E]

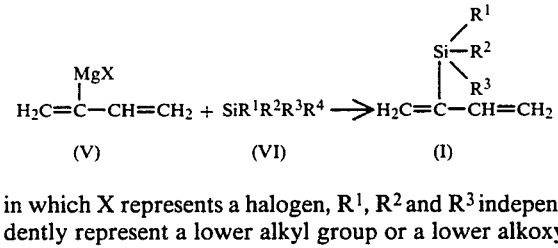

in which X represents a halogen, $R^1$, $R^2$ and $R^3$ independently represent a lower alkyl group or a lower alkoxy group with the exception of those compounds wherein $R^1$, $R^2$ and $R^3$ are all lower alkyl groups, and $R^4$ represents a halogen or a lower alkoxy group.

Specific examples of the magnesium 2-substituted-1,3-butadienyl halide of the formula (V) include Grignard reagents such as of chloroprene, bromoprene, 2,3-dichloro-1,3-butadiene, and the like. These Grignard reagents may be prepared by any ordinary procedures such as described, for example, in "Journal of Organic Chemistry, Vol. 44, page 4788(1979)".

The silane compounds of the formula (VI) are, for example, tetramethoxysilane, tetrabutoxysilane, trimethoxychlorosilane, tributoxybromosilane, trimethoxymethylsilane, tributoxybutylsilane, dimethoxydichlorosilane, dibutoxydibromosilane, dimethoxydimethylsilane, dibutoxydibutylsilane, dimethoxymethylchlorosilane, dibutoxybutylbromosilane, methoxytrichlorosilane, butoxytribromosilane, methoxytrimethylsiane, butoxytributylsilane, butoxydichloromethylsilane, butoxydibromobutylsilane, methoxychlorodimethylsilane, butoxybromodibutylsilane, tetrachlorosilane, tetrabromosilane, trichloromethylsilane, tribromobutylsilane, dichlorodimethylsilane, dibromodibutylsilane, chlorotrimethylsilane, bromotributylsilane, tetramethylsilane, tetrabutylsilane, and the like.

The reaction between the Grignard reagent of the formula (V) and the silane compound of the formula (VI) is carried out by a procedure which comprises dissolving the Grignard reagent in a solvent such as tetrahydrofuran, preferably cooling the solution to below room temperature, and subjecting to reaction with the silane compound in an atmosphere of an inert gas. The reaction temperature is preferably in the range of $-50°$ C. to a boiling point of the solvent used, most preferably in the range of 0° C. to room temperature. The reaction time is in the range of from 10 minutes to 5 hours, preferably from 30 minutes to 2 hours. The molar ratio of the Grignard reagent and the silane compound is from 1:0.2 to 1:5, preferably from 1:1 to 1:2. Aside from tetrahydrofuran, solvents which do not impede the reaction may be used singly or in combination with tetrahydrofuran. It will be noted that the degree of dilution of the reaction solution is conveniently determined in view of the heat of reaction and the volumetric efficiency.

The reaction between the Grignard reagent and the silane compound is ordinarily caused to proceed in an atmosphere of an inert gas. Examples of such inert gas include argon, helium, nitrogen and the like, which may be used singly or in combination. Of these, argon is preferred.

If the 2-substituted-1,3-butadiene produced by the above reaction is the compound of the formula (Ia), the compound of the formula (Ia) is reacted with a lower alcohol according to the reaction formula (C), as indicated before, preferably in the presence of a base including an organic aliphatic amine such as triethylamine in a non-alcoholic solvent such as tetrahydrofuran, by which the reaction proceeds smoothly. By the reaction, the halogen atom joined to the silane group is readily substituted with a lower alkoxy group to give the compound of the formula (Ib) according to the following reaction formula

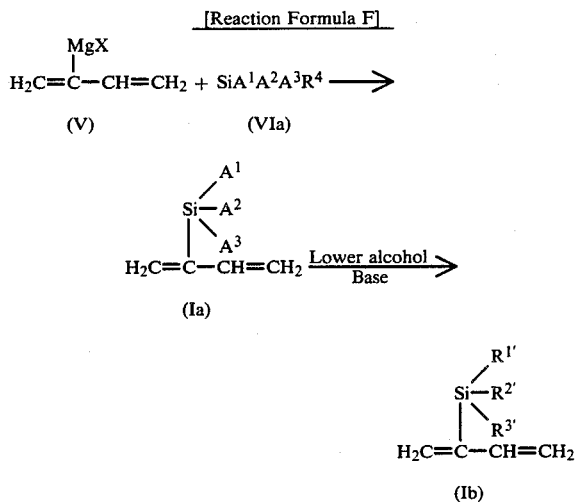

Note: $A^1$, $A^2$, $A^3$ and $R^4$ have, respectively, the same meanings as defined above.

According to the process of the invention which makes use of readily preparable magnesium substituted-1,3-butadienyl halides and silane compounds as starting materials, the reaction can be easily controlled with a reduced number of steps, so that substituted-1,3-butadiene derivatives can be economically prepared.

The present invention is described by way of examples, which should not be construed as limiting the present invention thereto.

EXAMPLE 1

[Preparation of 1,4-Dichloro-2-(trichloro)silyl-2-butene]

To a mixture of 15 ml (0.153 mol) of 1,4-dichloro-2-butyne and 13.6 ml (0.16 mol) of trichlorosilane (boiling point: 31°-32° C.) was added 0.15 ml (10 mmol) of an isopropyl alcohol solution of $H_2PtCl_6 \cdot 6H_2O$ (0.05 g/ml), followed by heating for 8 hours. Thereafter, the mixture was directly distilled to obtain 37 g of 1,4-dichloro-2-(trichloro)silyl-2-butene. Yield: 94%. Boiling point: 70° C./1 mmHg.

$^1$H NMR (CCl$_4$) using tetramethylsilane as the internal standard: $\delta$4.23 (d, J=7.5 Hz, 2H, C$\underline{H}_2$CH), 4.24 (s, 2H, C$\underline{H}_2$C), 6.66 (t, J=7.5 Hz, 1H, C$\underline{H}$CH$_2$).

[Preparation of 1,4-Dichloro-2-(trimethoxy)silyl-2-butene]

Seven milliliters of a THF solution of 14.2 g (55 mmols) of 1,4-dichloro-2-(trichloro)silyl-2-butene was cooled to $-10°$ C., into which was gently dropped a mixed solution of 10 ml (55×3×1.5 mmols) of CH$_3$OH and 34.5 ml (55×3×1.5 mmols) of (C$_2$H$_5$)$_3$N. Subsequently, the mixture was agitated for 1 hour, to which was added 30 ml of dried ether. The resulting (C$_2$H$_5$)$_3$N.HCl was removed by filtration and the solvent was distilled off under a reduced pressure and subjected to vacuum distillation to obtain 10.8 g of 1,4-dichloro-2-(trimethoxy) silyl-2-butene.

Yield: 80%. Boiling point: 88°-90° C./1-2 mmHg.

$^1$H NMR (CCl$_4$) using tetramethylsilane as the internal standard: $\delta$3.56 (s, 9H, CH$_3$O), 4.08 (s, 2H, CH$_3$C), 4.15 (d, J=7.5 Hz, 2H, C$\underline{H}_2$C$\underline{H}$), 6.29 (t, J=7.5 Hz, 1H, C$\underline{H}$CH$_2$)

[Preparation of 2-(Trimethoxy)silyl-1,3-butadiene]

Four grams (41×1.5 mmols) of Zn powder and 15 ml of THF were added, under agitation, to 10 g (41 mmols) of the 1,4-dichloro-2-(trimethoxy)silyl-2-butene obtained by the above procedure. The mixed solution was heated and refluxed for 1 hour and then cooled down to room temperature, followed by adding 30 ml of dried pentane. The resulting ZnCl$_2$ was removed by filtration and the solvent was distilled off under reduced pressure, followed by vacuum distillation to obtain 5.0 g of 2-(trimethoxy) silyl-1,3-butadiene.

Yield: 70%. Boiling point: 24° C./1 mmHg.

$^1$H NMR (CCl$_4$) using tetramethylsilane as the internal standard: $\delta$3.49 (s, 9H, CH$_3$O), 5.02 (d, J=10.8 Hz, 1H, C$\underline{H}_2$CH), 5.34 (d, J=17 Hz, 1H, C$\underline{H}_2$CH), 5.64 (d, J=3.3 Hz, 1H, C$\underline{H}_2$C), 5.77 (d, J=3.3 Hz, 1H, C$\underline{H}_2$C), 6.30 (dd, J=10.8, 17 Hz, 1H, C$\underline{H}$CH$_2$).

EXAMPLE 2

[Preparation of 2-(Trichloro)silyl-1,3-butadiene]

A mixture of 0.9 g (82×1.3 mmols) of Zn powder and 20 ml of THF was cooled to $-15°$ C., into which a mixture of 21.3 g (82 mmols) of 1,4-dichloro-2-(trichloro)silyl-2-butene and 10 ml of THF was gently dropped while agitating. Thereafter, the mixture was agitated at −15° C. for 1 hour, followed by adding 60 ml of dried pentane. The resulting $ZnCl_2$ was removed by filtration and the solvent was distilled off under reduced pressure at a low temperature of −20° C. to obtain 13 g of 2-(trichloro)silyl-1,3-butadiene.

Yield: 85%.

$^1$H NMR ($CCl_4$) using tetramethylsilane as the internal standard: δ5.30 (d, J=10.3 Hz, 1H, $CH_2C\underline{H}$), 5.56 (d, J=17.3 Hz, 1H, $C\underline{H}_2CH$), 6.04 (s, 2H, $\underline{CH}_2C$), 6.40 (dd, J=10.3, 17.3 Hz, 1H, $C\underline{H}CH_2$).

EXAMPLE 3

[Preparation of 2-(Trimethoxy)silyl-1,3-butadiene]

A mixture of 8.7 g (46 mmols of crude product) of 2-(trichloro)silyl-1,3-butadiene and 10 ml of THF was cooled down to −10° C., into which was gently dropped a mixture of 8.3 ml (46×31.5 mmols) of $CH_3OH$ and 28.9 ml (46×3×1.5 mmols) of $(C_2H_5)_3N$ while agitating. Thereafter, the mixture was agitated at room temperature for further 30 minutes, followed by adding 30 ml of $(C_2H_5)_2O$. The resulting $(C_2H_5)_3N.HCl$ was removed by filtration and the solvent was distilled off under reduced pressure, followed by vacuum distillation to obtain 6.1 g of 2-(trimethoxy)silyl-1,3-butadiene. Yield: 75%.

The boiling point and $^1$H NMR were found to be the same as in the case of Example 1.

EXAMPLE 4

[Preparation of 1,4-Dichloro-2-(chlorodimethyl)silyl-2-butene]

To a mixture of 11 ml (0.116 mol) of 1,4-dichloro-2-butyne and 13.5 ml (0.12 mol) of chlorodimethylsilane (boiling point: 35° C.) was added 0.05 ml (4.4 mmols) of an isopropanol solution of chloroplatinic acid prepared in the same manner as in Example 1, followed by heating under reflux for 30 minutes, thereby obtaining 23 g of 1,4-dichloro-2-(chlorodimethyl)silyl-2-butene.

Yield: 91%. Boiling point: 68° C./1 mmHg.

$^1$H NMR ($CCl_4$) using benzene as the internal standard: δ0.57 (s, 6H, $CH_3Si$), 4.11 (d, J=7.5 Hz, 2H, $C\underline{H}_2CH$), 4.16 (s, 2H, $\underline{CH}_2C$), 6.19 (t, J=7.5 Hz, 1H, $C\underline{H}CH_2$).

[Preparation of 1,4-Dichloro-2-(methoxydimethyl)silyl-2-butene]

13.3 g (61 mmols) of 1,4-dichloro-2-(chlorodimethyl) silyl-2-butene, 10 ml of THF, 3.7 ml of $CH_3OH$ (61×1.5 mmols), 12.7 ml (61×1.5 mmols) of $(C_2H_5)_3N$, and 30 ml of dried ether were used and subjected to vacuum distillation, thereby obtaining 10.5 g of 1,4-dichloro-2-(methoxydimethyl)silyl-2-butene.

Yield: 81%. Boiling point: 74° C./1 mmHg.

$^1$H NMR ($CCl_4$) using benzene as the internal standard: δ0.28 (s, 6H, $CH_3Si$), 3.39 (s, 3H, $CH_3O$), 4.11 (s, 2H, $\underline{CH}_2C$), 4.14 (d, J=7.3 Hz, 2H, $C\underline{H}_2CH$), 6.09 (t, J=7.3 Hz, 1H, $C\underline{H}CH_2$).

[Preparation of 2-(Methoxydimethyl)silyl-1,3-butadiene]

While 4.0 g (41×1.5 mmols) of Zn powder and 15 ml of THF were agitated, 8.7 g (41 mmols) of 1,4-dichloro-2-(methoxydimethyl)silyl-2-butene was added. The mixture was heated under reflux for 2 hours, and then treated in the same manner as in Example 1 to obtain 4.4 g of 2-(methoxydimethyl)silyl-1,3-butadiene.

Yield: 76%. Boiling point: 30° C./10–12 mmHg.

$^1$H NMR ($CCl_4$) using benzene as the internal standard: δ0.20 (s, 6H, $CH_3Si$), 3.34 (s, 3H, $CH_3O$), 5.01 (d, J=10 Hz, 1H, $C\underline{H}_2CH$), 5.32 (d, J=17.3 Hz, 1H, $C\underline{H}_2CH$), 5.43 (d, J=3 Hz, 1H, $C\underline{H}_2C$), 5.69 (d, J=3 Hz, 1H, $C\underline{H}_2C$), 6.33 (dd, J=10, 17.3 Hz, 1H, $C\underline{H}CH_2$).

EXAMPLE 5

[Preparation of 2-(Dimethylchloro)silyl-1,3-butadiene]

A mixture of 2.4 g (28×1.3 mmols) of Zn powder and 4 ml of THF as cooled down to 0° C., into which was gently dropped, under agitation, a mixture of 6.1 g (28 mmols) of 1,4-dichloro-2-(chlorodimethyl)silyl-2-butene and 3 ml of THF. Thereafter, the mixture was well agitated at 0° C. for 5 hours, followed by adding 15 ml of dried pentane and removing the resulting $ZnCl_2$ by filtration. The solvent was distilled off under reduced pressure at a low temperature of −20° C. and the residue was subjected to the bulb-to-bulb distillation to obtain 3.1 g of 2-(dimethylchloro)silyl-1,3-butadiene.

Yield: 68%. Boiling point: 57° C./1 mmHg.

$^1$H NMR ($CCl_4$) using benzene as the internal standard: δ0.57 (s, 6H, $CH_3Si$), 5.10 (d, J=10.8 Hz, 1H, $C\underline{H}_2CH$), 5.32 (d, J=17.5 Hz, 1H, $C\underline{H}_2CH$), 5.61 (d, J=2.5 Hz, 1H, $C\underline{H}_2C$), 5.80 (d, J=2.5 Hz, 1H, $C\underline{H}_2C$), 6.37 (dd, J=10.8, 17.5 Hz, 1H, $C\underline{H}_2CH$).

EXAMPLE 6

[Preparation of 2-(Ethoxydimethyl)silyl-1,3-butadiene]

0.88 g (6 mmols) of 2-(dimethylchloro)silyl-1,3-butadiene, 5 ml of THF, 0.53 ml (6×1.5 mmols) of $C_2H_5OH$, 1.3 ml (6×1.5 mmols) of $(C_2H_5)_3N$, and 10 ml of $(C_2H_5)_2O$ were used and treated in the same manner as in Example 3, followed by subjecting to the silica gel column chromatography (using pentane alone), thereby obtaining 0.8 g of 2-(ethoxydimethyl)silyl-1,3-butadiene. Yield: 86%.

$^1$H NMR ($CCl_4$) using benzene as the internal standard: δ0.23 (s, 6H, $CH_3Si$), 1.14 (t, J=6.8 Hz, 3H, $CH_3CH_2$), 3.58 (q, 2H, $\underline{CH}_2CH_3$), 5.01 (d, J=10.3 Hz, 1H, $C\underline{H}_2CH$), 5.33 (d, J=17.3 Hz, 1H, $C\underline{H}_2CH$), 5.42 (d, J=3 Hz, 1H, $C\underline{H}_2C$), 5.67 (d, J=3 Hz, 1H, $C\underline{H}_2C$), 6.33 (dd, J=10.3, 17.3 Hz, 1H, $C\underline{H}CH_2$).

EXAMPLE 7

[Preparation of 1,4-Dichloro-2-(dichloromethyl)silyl-2-butene]

To a mixture of 10 ml (0.106 mol) of 1,4-dichloro-2-butyne and 11.5 ml (0.11 mol) of dichloromethylsilane (boiling point: 41° C.) was added 0.05 ml (4.8 mmol %) of an isopropanol solution of chloroplatinic acid prepared in the same manner as in Example 1, followed by heating under reflux for 1 hour, thereby obtaining 22 g of 1,4-dichloro-2-(dichloromethyl)silyl-2-butene.

Yield: 87%. Boiling point: 57° C./1 mmHg.

$^1$H NMR ($CCl_4$) using tetramethylsilane as the internal standard: δ0.96 (s, 3H, $CH_3Si$), 4.19 (d, J=7.5 Hz, 2H, $C\underline{H}_2CH$), 4.24 (s, 2H, $C\underline{H}_2C$), 6.49 (t, J=7.5 Hz, 1H, $C\underline{H}CH_2$).

[Preparation of 1,4-Dichloro-2-(dimethoxymethyl)silyl-2-butene]

11.5 g (48 mmols) of 1,4-dichloro-2-(dichloromethyl)-silyl-2-butene, 1.0 ml of THF, 5.9 ml (48×2×1.5 mmols) of CH$_3$OH, 20 ml (48×2×1.5 mmols) of (C$_2$H$_5$)$_3$N, and 30 ml of (C$_2$H$_5$)$_2$O were used and subjected to vacuum distillation, thereby obtaining 8.8 g of 1,4-dichloro-2-(dimethoxymethyl)silyl-2-butene.

Yield: 80%. Boiling point: 63° C./1 mmHg.

$^1$H NMR (CCl$_4$) using tetramethylsilane as the internal standard: δ0.24 (s, 3H, C$\underline{H}_3$Si), 3.48 (s, 6H, C$\underline{H}_3$O), 4.10 (s, 2H, C$\underline{H}_2$C), 4.14 (d, J=7.5 Hz, 2H, C$\underline{H}_2$CH), 6.19 (t, J=7.5 Hz, 1H, C$\underline{H}$CH$_2$).

[Preparation of 2-(Dimethoxymethyl)silyl-1,3-butadiene]

While 3.5 g (35×1.5 mmols) of Zn powder and 15 ml of THF were agitated, 8.0 g (35 mmols) of 1,4-dichloro-2-(dimethoxymethyl)silyl-2-butene was added. The mixture was heated under reflux for 2 hours, and then treated in the same manner as in Example 1 to obtain 3.9 g of 2-(dimethoxymethyl)silyl-1,3-butadiene.

Yield: 71%. Boiling point: 31° C./10–12 mmHg.

$^1$H NMR (CCl$_4$) using tetramethylsilane as the internal standard: δ0.17 (s, 3H, C$\underline{H}_3$Si), 3.42 (s, 6H, C$\underline{H}_3$O), 5.00 (d, J=10.3 Hz, 1H, C$\underline{H}_2$CH), 5.33 (d, J=17.8 Hz, 1H, C$\underline{H}_2$CH), 5.58 (d, J=3.8 Hz, 1H, C$\underline{H}_2$C), 5.73 (d, J=3.8 Hz, 1H, C$\underline{H}_2$C), 6.32 (dd, J=10.3, 17.8 Hz, 1H, C$\underline{H}$CH$_2$).

EXAMPLE 8

Into a reactor were charged 4.0 g (0.15 mol) of metallic magnesium, 4 ml of dried tetrahydrofuran, and 1 ml of dried dibromoethane, whereupon heat generated with the tetrahydrofuran being refluxed. After completion of the heat generation, zinc chloride was added in an amount of 2 mol % based on chloroprene being reacted, followed by further adding 50 ml of dried tetrahydrofuran.

Subsequently, a mixture of 10 ml (0.1 mol) of chloroprene, 40 ml of dried tetrahydrofuran, and 1.8 ml of dibromoethane was added in about 30 minutes to cause the reaction to proceed. Generation of heat took place and the tetrahydrofuran started to be refluxed, followed by further reaction for 1 hour, thereby forming magnesium 2-(1,3-butadienyl)chloride in the tetrahydrofuran solution.

The content of the product was determined as follows: the magnesium 2-(1,3-butadienyl)chloride was hydrolyzed using water and an excess of hydrochloric acid, followed by back titration of the hydrochloric acid with an aqueous caustic soda solution.

Twenty milliliters of the thus obtained tetrahydrofuran solution of 20 mmols of magnesium 2-(1,3-butadienyl)chloride was charged into a reactor in the stream of argon. Thereafter, the reactor was cooled to 0° C., to which was gently added 1.4 ml (10 mmols) of tetramethoxysilane, followed by reaction at room temperature for 1 hour. After completion of the reaction, the solvent was distilled off, thereby obtaining 2-(trimethoxy) silyl-1,3-butadiene. The yield calculated from the result of gas chromatography was 30%. The boiling point and $^1$H NMR (CCl$_4$) were the same as in the case of Example 1.

EXAMPLE 9

4.1 ml of the tetrahydrofuran solution of magnesium 2-(1,3-butadienyl)chloride (4.0 mmols) obtained in Example 8 and 6 ml of dried tetrahydrofuran were charged into a reactor in the stream of argon. Subsequently, the reactor was cooled down to 0° C., followed by gentle dropping of 0.6 ml (4 mmols) of tetrahydrofuran. Thereafter, the reaction was effected at room temperature for 1 hour. After completion of the reaction, the solvent was distilled off to obtain 2-(trimethoxy)silyl-1,3-butadiene (yield: 35%).

EXAMPLE 10

4.1 ml of the tetrahydrofuran solution of magnesium 2-(1,3-butadienyl)chloride and 6 ml of dried tetrahydrofuran were charged into a reactor in the stream of argon. Subsequently, the reactor was cooled down to 0° C., followed by gentle dropping of 1.2 ml (8 mmols) of tetramethoxysilane. While the reaction temperature was kept at 0° C., the reaction was continued for 30 minutes. After completion of the reaction, the solvent was distilled off to obtain 2-(trimethoxy)silyl-1,3-butadiene (yield: 65%).

What is claimed is:

1. A 2-substituted-1,3-butadiene compound of the formula (I)

in which R$^1$, R$^2$ and R$^3$ are independently selected from the group consisting of a lower alkyl group and a lower alkoxy group, with the proviso that R$^1$, R$^2$ and R$^3$ are not all a lower alkyl group.

2. The compound of claim 1, which is 2-(trimethoxy)-silyl-1,3-butadiene.

3. The compound of claim 1, which is 2-(methoxydimethyl)silyl-1,3-butadiene.

4. The compound of claim 1, which is 2-(dimethoxymethyl)silyl-1,3-butadiene.

5. The compound of claim 1, wherein only one of R$^1$, R$^2$ and R$^3$ is a lower alkoxy group.

6. The compound of claim 1, wherein only two of R$^1$, R$^2$ and R$^3$ are a lower alkoxy group.

7. The compound of claim 1, wherein R$^1$, R$^2$ and R$^3$ are each a lower alkoxy group.

8. A 2-substituted-1,3-butadiene compound of the formula (I)

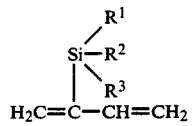

in which R$^1$ is a lower alkoxy group and R$^2$ and R$^3$ are selected from the group consisting of lower alkyl groups, lower alkoxy groups and halogens.

9. The compound of claim 8, wherein only one of R$^1$, R$^2$ and R$^3$ is a lower alkoxy group.

10. The compound of claim 8, wherein only two of R$^1$, R$^2$ and R$^3$ are a lower alkoxy group.

* * * * *